United States Patent
Tran et al.

(10) Patent No.: US 7,922,663 B2
(45) Date of Patent: Apr. 12, 2011

(54) IMPLANTABLE ULTRASOUND SYSTEM FOR MAINTAINING VESSEL PATENCY AND PERFUSION

(75) Inventors: Binh C. Tran, Minneapolis, MN (US); Abhi Chavan, Maple Grove, MN (US); Rodney W. Salo, Fridley, MN (US); Jonathan Kwok, Denville, NJ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 784 days.

(21) Appl. No.: 11/903,735

(22) Filed: Sep. 24, 2007

(65) Prior Publication Data
US 2009/0082781 A1 Mar. 26, 2009

(51) Int. Cl.
*A61B 8/00* (2006.01)

(52) U.S. Cl. ............................................. 600/459; 607/4

(58) Field of Classification Search .................. 600/459, 600/462–469, 481, 485–488; 604/22; 601/2; 607/4–8
See application file for complete search history.

(56) References Cited

U.S. PATENT DOCUMENTS

| | | |
|---|---|---|
| 4,432,374 A | 2/1984 | Osanai |
| 4,798,211 A | 1/1989 | Goor et al. |
| 4,821,735 A | 4/1989 | Goor et al. |
| 5,113,869 A | 5/1992 | Nappholz et al. |
| 5,188,106 A | 2/1993 | Nappholz et al. |
| 5,228,449 A | 7/1993 | Christ et al. |
| 5,305,745 A | 4/1994 | Zacouto |
| 6,021,350 A | 2/2000 | Mathson |
| 6,152,882 A | 11/2000 | Prutchi |
| 6,233,486 B1 | 5/2001 | Ekwall et al. |
| 6,237,398 B1 | 5/2001 | Porat et al. |
| 6,319,205 B1 | 11/2001 | Goor et al. |
| 6,368,284 B1 | 4/2002 | Bardy |
| 6,421,565 B1 | 7/2002 | Hemmingsson |
| 6,468,219 B1 | 10/2002 | Njemanze |
| 6,480,733 B1 | 11/2002 | Turcott |
| 6,520,916 B1 | 2/2003 | Brennen |
| 6,527,729 B1 | 3/2003 | Turcott |
| 6,575,922 B1 | 6/2003 | Fearnside et al. |
| 6,600,949 B1 | 7/2003 | Turcott |
| 6,604,000 B2 | 8/2003 | Lu |
| 6,733,450 B1 * | 5/2004 | Alexandrov et al. ......... 600/439 |

(Continued)

FOREIGN PATENT DOCUMENTS

| | | |
|---|---|---|
| EP | 348271 | 12/1989 |
| EP | 1175920 | 1/2002 |
| WO | WO-00/27293 A1 | 5/2000 |
| WO | WO-03/068047 A2 | 8/2003 |
| WO | WO-2009042141 A1 | 4/2009 |

OTHER PUBLICATIONS

"International Application Serial No. PCT/US2008/011058, International Search Report mailed Jan. 27, 2009", 5 pgs.

(Continued)

*Primary Examiner* — Brian Casler
*Assistant Examiner* — Parikha S Mehta
(74) *Attorney, Agent, or Firm* — Schwegman, Lundberg & Woessner, P.A.

(57) ABSTRACT

An apparatus comprising an implantable acoustic transducer, an acoustic transducer interface circuit communicatively coupled to the acoustic transducer, and a controller circuit communicatively coupled to the acoustic transducer interface circuit. The controller is configured to, in response to receiving an indication of a patient condition associated with a development of a blood vessel obstruction, initiate delivery of acoustic energy that mitigates the blood vessel obstruction. Other systems and methods are described.

25 Claims, 10 Drawing Sheets

U.S. PATENT DOCUMENTS

| | | |
|---|---|---|
| 6,827,690 B2 | 12/2004 | Bardy |
| 6,942,622 B1 | 9/2005 | Turcott |
| 7,035,684 B2 | 4/2006 | Lee |
| 7,037,266 B2 | 5/2006 | Ferek-Petric et al. |
| 7,177,686 B1 | 2/2007 | Turcott |
| 7,206,636 B1 | 4/2007 | Turcott |
| 7,299,087 B2 | 11/2007 | Bardy |
| 7,577,478 B1 | 8/2009 | Kroll et al. |
| 2003/0004549 A1 | 1/2003 | Hill et al. |
| 2005/0209578 A1 | 9/2005 | Christian Evans et al. |
| 2005/0283195 A1 | 12/2005 | Pastore et al. |
| 2006/0259087 A1 | 11/2006 | Baynham et al. |
| 2006/0287684 A1 | 12/2006 | Baynham et al. |
| 2007/0043393 A1 | 2/2007 | Brockway et al. |
| 2007/0054871 A1 | 3/2007 | Pastore et al. |
| 2007/0150005 A1 | 6/2007 | Sih et al. |
| 2007/0150015 A1 | 6/2007 | Zhang et al. |
| 2007/0276453 A1 | 11/2007 | Hill et al. |
| 2007/0299356 A1 | 12/2007 | Wariar et al. |
| 2008/0058661 A1 | 3/2008 | Bardy |
| 2008/0177156 A1 | 7/2008 | Zhang et al. |
| 2008/0177194 A1 | 7/2008 | Zhang et al. |
| 2009/0025459 A1 | 1/2009 | Zhang et al. |
| 2009/0171228 A1 | 7/2009 | Fischell et al. |

OTHER PUBLICATIONS

"International Application Serial No. PCT/US2008/011058, Written Opinion mailed Jan. 27, 2009", 8 pgs.

Iida, K., et al., "Noninvasive low-frequency ultrasound energy causes vasodilation in humans.", *J Am Coll Cardiol.*, 48(3), (Aug. 1, 2006),532-7.

Miyamoto, T., et al., "Coronary Vasodilation by Noninvasive Transcutaneous Ultrasound", *Journal of the American College of Cardiology*, 41(9), (2003),1623-1628.

Ni, Q., et al., "Closed-Loop Resynchronization Therapy for Mechanical Dyssynchrony", U.S. Appl. No. 11/690,700, filed Mar. 23, 2007, 32 pages.

Siegel, R. J., et al., "Noninvasive, transthoracic, low-frequency ultrasound augments thrombolysis in a canine model of acute myocardial infarction.", *Circulation* 101(17), (May 2, 2000), 2026-9.

Siegel, R. J., et al., "Ultrasound energy improves myocardial perfusion in the presence of coronary occlusion.", *J Am Coll Cardiol.*, 44(7):, (Oct. 6, 2004), 1454-1458.

Suchkova, V., et al., "Effect of 40-kHz ultrasound on acute thrombotic ischemia in a rabbit femoral artery thrombosis model: enhancement of thrombolysis and improvement in capillary muscle perfusion", *Circulation*, 101(19), (May 16, 2000),2296-301.

Suchkova, V., et al., "Enhancement of Fibrinolysis With 40-kHz Ultrasound", *Circulation*, 98(10), (1998),1030-1035.

Suchkova, V., et al., "Ultrasound enhancement of fibrinolysis at frequencies of 27 to 100 kHz.", *Ultrasound Med Biol.*, 28(3), (Mar. 2002),377-82.

Zhang, Y., et al., "Heart Attack Detector", U.S. Appl. No. 11/625,045, filed Jan. 19, 2007, 46 pages.

\* cited by examiner

IMPLANTABLE ULTRASOUND SYSTEM FOR MAINTAINING VESSEL PATENCY AND PERFUSION

FIELD OF THE INVENTION

The field generally relates to implantable medical devices and, in particular, but not by way of limitation, to systems, devices, and methods to restore or promote adequate blood flow in blood vessels.

BACKGROUND

Implantable medical devices (IMDs) include devices designed to be implanted into a patient. The devices can be used to treat patients using electrical or other therapy or to aid a physician or caregiver in patient diagnosis through internal monitoring of a patient's condition. Thrombosis is an obstruction of an artery or vein by a blood clot or thrombus. Thrombosis may result in ischemia. Thrombosis may occur in patients who develop atherosclerosis or have coronary artery disease (CAD), heart failure (HF), atrial fibrillation (AF), stroke, or other medical situations. Some clinical interventions, such as a stent procedure or treatment of anemia in HF patients, increase the risk of thrombosis. Vasoconstriction is an obstruction of an artery or vein due to a decrease in the diameter of blood vessels. Vasoconstriction may also result in ischemia. It is desirable to mitigate blood vessel obstructions or the risk of obstructions and to restore or promote adequate blood flow in blood vessels.

OVERVIEW

This document relates generally to systems, devices, and methods for providing cardiac therapy to a subject. In example 1, an apparatus includes an implantable acoustic transducer, an acoustic transducer interface circuit communicatively coupled to the acoustic transducer, and a controller circuit communicatively coupled to the acoustic transducer interface circuit. The controller circuit is configured to, in response to receiving an indication of a patient condition associated with a development of a blood vessel obstruction, initiate delivery of acoustic energy that mitigates the blood vessel obstruction.

In example 2, the apparatus of example 1 optionally includes an atrial fibrillation detection circuit communicatively coupled to the controller circuit to provide the indication upon detecting atrial fibrillation.

In example 3, the apparatus of examples 1 and 2 optionally includes an ischemia detection circuit communicatively coupled to the controller circuit to provide the indication upon detecting ischemia.

In example 4, the controller circuit of examples 1-3 optionally is optionally configured to initiate the application of acoustic energy at a first frequency to detect the patient condition, and initiate the application of acoustic energy at a lower second frequency to mitigate the blood vessel obstruction in response to receiving the indication.

In example 5, the apparatus of example 4 optionally includes a blood flow velocity measurement circuit configured to receive ultrasonic information using ultrasonic energy at the first frequency, and generate a blood flow velocity measurement from the ultrasonic information. The indication includes a blood flow velocity measurement that is less than a blood flow velocity threshold.

In example 6, the apparatus of examples 1-5 is optionally includes a detection circuit coupled to the controller circuit. The detection circuit is optionally configured to detect an indication of a patient condition associated with a development of a blood vessel obstruction, and the controller circuit is optionally configured to apply the acoustic energy while the detection circuit indicates the patient condition.

In example 7, the apparatus of examples 1-6 optionally includes a communication circuit communicatively coupled to the controller circuit. The controller circuit is optionally configured to communicate with a separate second device using the communication circuit and to receive the indication from the separate second device.

In example 8, the indication of example 7 optionally includes at least one of an increase in blood viscosity, thrombosis, atrial fibrillation, ischemia, a decrease in blood velocity, and a decrease in local perfusion.

In example 9, the acoustic transducer of examples 1-8 is optionally included in an implantable lead. The implantable lead is optionally configured for placement in or near a blood vessel.

In example 10, the acoustic transducer of examples 1-9 is optionally included in an implantable lead and optionally configured for placement in or near a localized region of a heart.

In example 11, the acoustic transducer of examples 1-10 is optionally included in a housing of the implantable medical device.

In example 12, the apparatus of claims 1-11 optionally includes an implantable lead configured for placement in or near a blood vessel, and the acoustic transducer is optionally included in a housing of the implantable medical device and delivers the acoustic energy towards the implantable lead.

In example 13, the implantable lead of example 12 optionally includes an acoustic energy sensor.

In example 14, the apparatus of example 13 optionally includes a placement guidewire configured for insertion into the implantable lead. The guidewire optionally includes an acoustic energy sensor.

In example 15, a method includes receiving an indication of a patient condition into an implantable medical device (IMD). The patient condition is associated with a development of a blood vessel obstruction. The method further includes applying, in response to receiving the indication of the patient condition, acoustic energy that mitigates the blood vessel obstruction using the IMD.

In example 16, the receiving the indication of a patient condition of example 15 optionally includes detecting atrial fibrillation using the IMD.

In example 17, the receiving the indication of a patient condition of examples 15-16 optionally includes detecting a decrease in blood flow velocity using the IMD.

In example 18, the receiving the indication of a patient condition of examples 15-17 optionally includes detecting ischemia using the IMD.

In example 19, the receiving the indication of a patient condition of examples 15-18 optionally includes receiving an indication of thrombosis.

In example 20, the receiving the indication of a patient condition of examples 15-19 optionally includes receiving an indication of an increase in blood viscosity.

In example 21, the receiving the indication of a patient condition of examples 15-20 optionally includes receiving an indication of a decrease in regional perfusion.

In example 22, the method of examples 15-21 optionally includes applying acoustic energy at a first frequency to detect the patient condition, and applying acoustic energy at a lower second frequency to mitigate the blood vessel obstruction when the patient condition is detected.

In example 23, the applying acoustic energy at a first frequency of example 22 optionally includes applying ultrasound energy at a frequency greater than two megahertz (2 MHz) to measure blood flow velocity, and the applying acoustic energy at a lower second frequency optionally includes applying ultrasound energy at a frequency of about 500 kilohertz (kHz) or less to mitigate the blood vessel obstruction.

In example 24, the applying acoustic energy of examples 15-23 optionally includes applying localized ultrasound energy to a blood vessel in the thorax region of the patient.

In example 25, the applying acoustic energy of examples 15-24 optionally includes applying ultrasound energy locally to a region of the heart.

In example 26, the applying acoustic energy of examples 15-25 optionally includes applying ultrasound energy globally to the thorax region.

In example 27, the applying acoustic energy of examples 15-26 optionally includes applying localized ultrasound energy to a region containing a second separate implantable device.

In example 28, the applying acoustic energy of examples 15-27 optionally includes initiating the applying acoustic energy by the implantable medical device using a separate second device.

In example 29, the receiving the indication of examples 15-28 optionally includes detecting the patient condition associated with a development of a blood vessel obstruction using the IMD, the applying acoustic energy optionally includes applying the acoustic energy in response to detecting the patient condition, and the method of examples 15-28 optionally includes continuing the applying acoustic energy while the detected condition is present.

This overview is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Ischemia is a deficiency of blood flow to a bodily organ or bodily tissue caused by a blood vessel obstruction such as an obstacle in a blood vessel or a constriction of a blood vessel. Ultrasound can be used to induce therapeutic pathways that may treat, reverse, and prevent ischemia. More specifically, ultrasound may be effective to dissolve thrombi (thrombolysis). Mechanical energy of relatively low frequency ultrasound (e.g. 20 kHz to 200 kHz) can break up thrombi. Low frequency ultrasound may be also effective to induce vasodilation to reverse vasoconstriction. This may be because of stimulation of endothelial mechanoreceptors and a subsequent release of nitric oxide.

Figure 1:
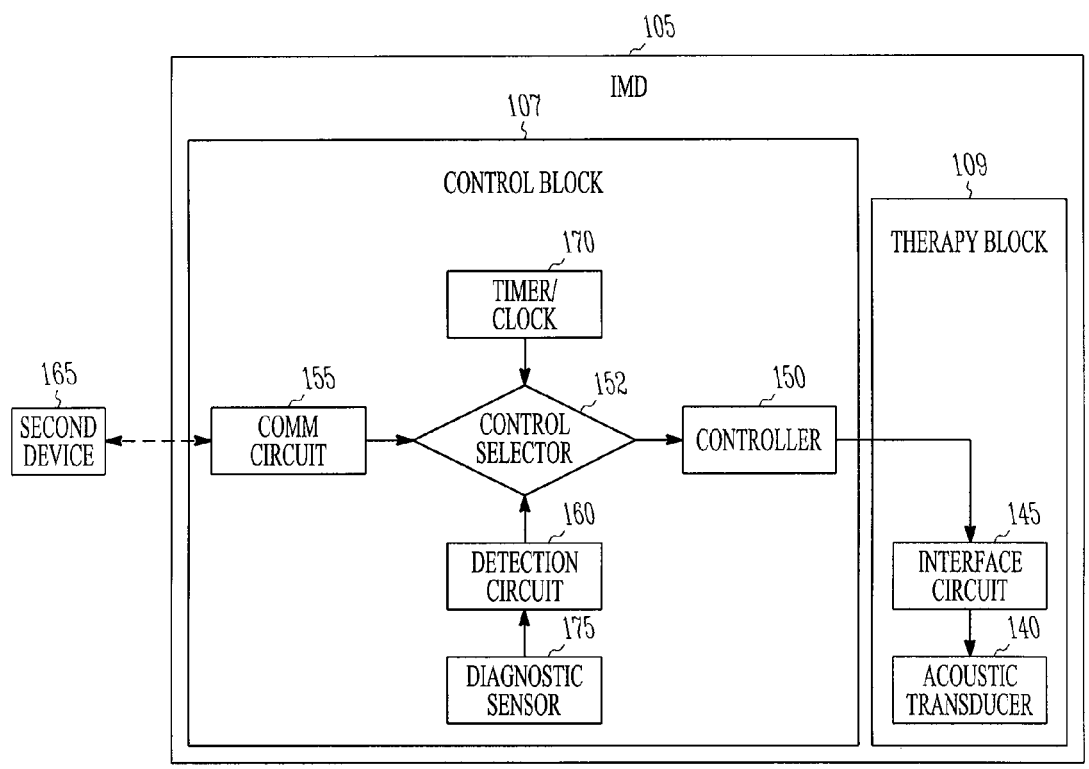
FIG. 1 is a block diagram of an example of portions of an implantable medical device (IMD), according to various embodiments of the invention.

FIG. 1 is a block diagram of an example of portions of an implantable medical device (IMD) 105 that includes a control block 107 and a therapy block 109. The therapy block 109 includes an implantable acoustic transducer 140, such as an ultrasonic transducer for example, and an acoustic transducer interface circuit 145. In some examples, the implantable acoustic transducer 140 is configured for placement in a thorax region of a patient. The acoustic transducer is configured to provide low frequency ultrasound energy. In some examples the acoustic transducer is configured to provide ultrasound energy having a frequency of about 500 kilohertz (kHz) or less. In some examples the acoustic transducer is configured to provide ultrasound energy having a frequency of about 200 kHz or less. In some examples the acoustic transducer is configured to provide ultrasound energy having a frequency of about 20 kHz to 100 kHz. Acoustic transducer interface circuit 145 provides an electrical signal to drive the transducer with the desired parameters, such as a desired frequency and/or a desired amplitude for example.

The control block 107 includes a controller circuit 150 configured to receive an indication of a patient condition associated with a development of a blood vessel obstruction, such as a thrombus or a vasoconstriction. In response to receiving the indication, the controller circuit 150 initiates delivery of acoustic energy that mitigates the blood vessel obstruction. The acoustic energy may be low frequency ultrasound energy to enhance thrombolysis, or to induce vasodilation. In some examples, the frequency of the acoustic energy is programmable. The acoustic energy may be continuous wave energy delivered for a period of time, or pulsed energy and have a programmable pulse duration and pulse repetition rate.

The IMD 105 is a chronic device that provides low frequency ultrasound therapy. If the patient is experiencing ischemia, the low frequency ultrasonic energy may elicit therapeutic pathways to restore adequate oxygen delivery to the effected tissue. These pathways may be restored due to dissolution of thrombi and/or triggering of a vasodilatory response. The occluded or partially occluded vessel is targeted with low frequency ultrasonic energy which may cause increased collateral circulation to mitigate the primary occlusion. Ultrasound having frequencies of 27 kHz to 100 kHz may enhance thrombolysis. Ultrasound at a frequency of 20 kHz may improve myocardial perfusion. It is to be noted that an actual thrombus or vasoconstriction does not need to be present for the IMD 105 to provide a benefit to the patient. The ultrasound energy may be delivered as preventive therapy to help prevent formation of a thrombus or a vasoconstriction in the vicinity of the acoustic transducer 140. Also, the ultrasound therapy may increase the effectiveness of drug therapy to prevent thrombus or vasoconstriction.

The controller circuit 150 may include a digital signal processor, application specific integrated circuit (ASIC), microprocessor, or other type of processor, interpreting or executing instructions in software or firmware. In some examples, the controller circuit 150 may include a state machine or sequencer that is implemented in hardware circuits. The controller circuit 150 may include any combination of hardware, firmware, or software. The controller circuit 150 can include one or more circuits to perform the functions described herein. A circuit may include software, hardware, firmware or any combination thereof. For example, the circuit may include instructions in software executing on or interpreted by the controller circuit 150. Multiple functions may be performed by one or more circuits.

In some examples, the IMD 105 includes a communication circuit 155 to provide communication with a separate second device 165, such as a second separate IMD or an external device. The controller circuit 150 communicates wirelessly with the second device 165 using the communication circuit 155, such as by using radio frequency (RF) or other telemetry method. The controller circuit 150 receives the indication of the patient condition from the second device 165.

In some examples, the IMD 105 includes a timer or clock circuit 170 as part of the controller circuit 150 or as a circuit separate from the controller circuit 150. The controller circuit 150 uses a signal received from the clock circuit to initiate delivery of the acoustic energy periodically, such as hourly or by time of day for example. In certain examples, once the controller circuit 150 receives an indication of the patient condition, the controller circuit initiates delivery of the acoustic energy periodically. The control selector 152 may receive the indication from the detection circuit 160, the communication circuit 155, or the clock circuit 170.

Figure 2:
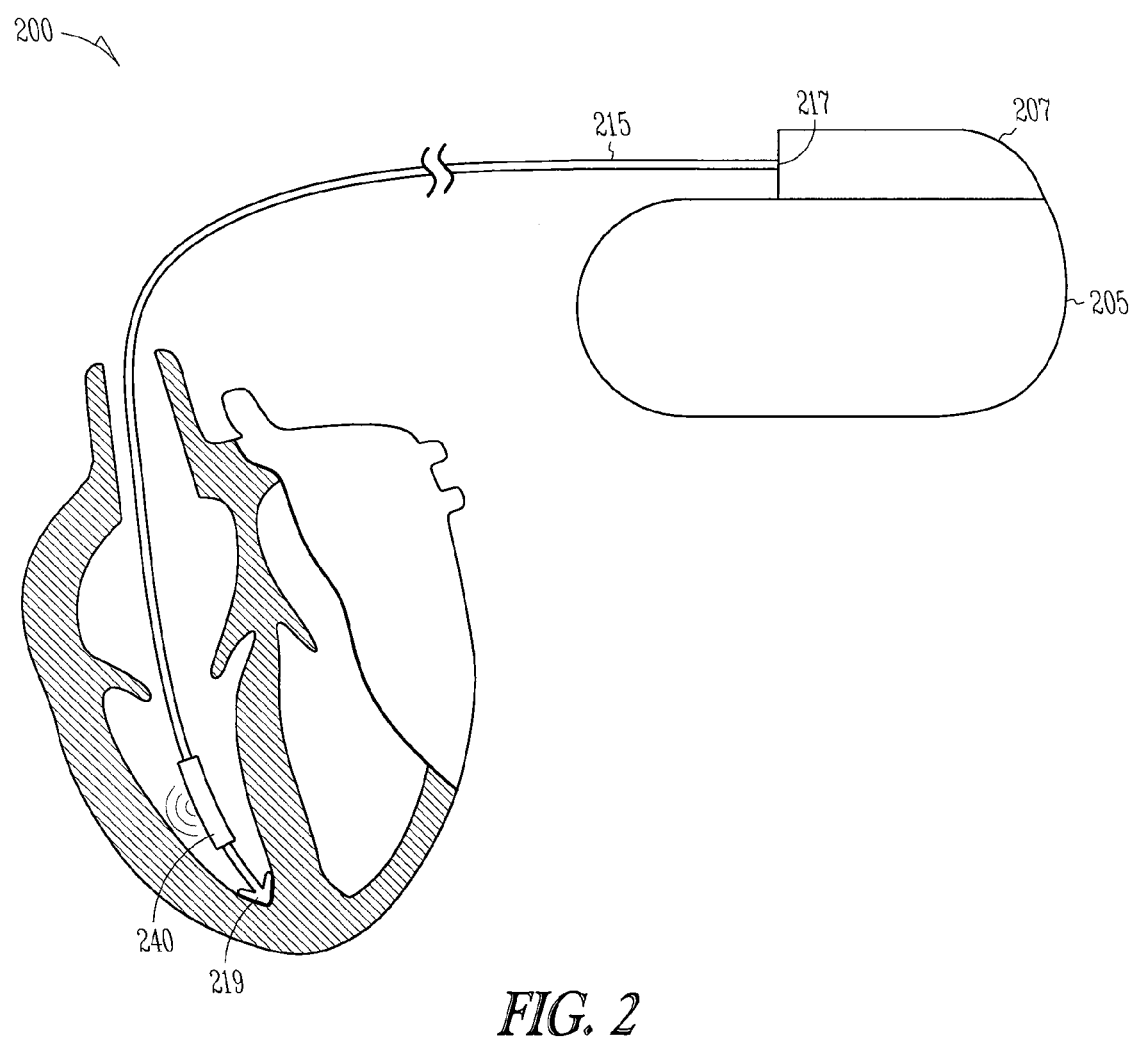
FIG. 2 is an illustration of portions of a system that includes an IMD.

FIG. 2 is an illustration of portions of an example of a system 200 that includes an IMD 205. The IMD 205 includes an electronics unit coupled by an implantable lead 215 to a heart of a patient or subject. The electronics unit is enclosed in a hermetically-sealed housing or "can." The implantable lead 215 is shaped and sized for placement in a right ventricle (RV) and has a proximal end 217 and a distal end 219. The proximal end 217 is coupled to a header connector 207 of the IMD 205. The implantable lead 215 includes an implantable acoustic transducer 240 near the distal end 219. In some examples, the implantable lead 215 may be configured for placement in another heart chamber such as the right atrium (RA). The acoustic transducer 240 applies ultrasound energy locally to a region of the heart. In the example shown, the acoustic transducer 240 applies localized low frequency ultrasound energy to a region near the apex of the RV. In some examples, the local region extends about 10 millimeters. In some examples, the acoustic transducer 240 is implanted in a blood vessel.

Figure 3:
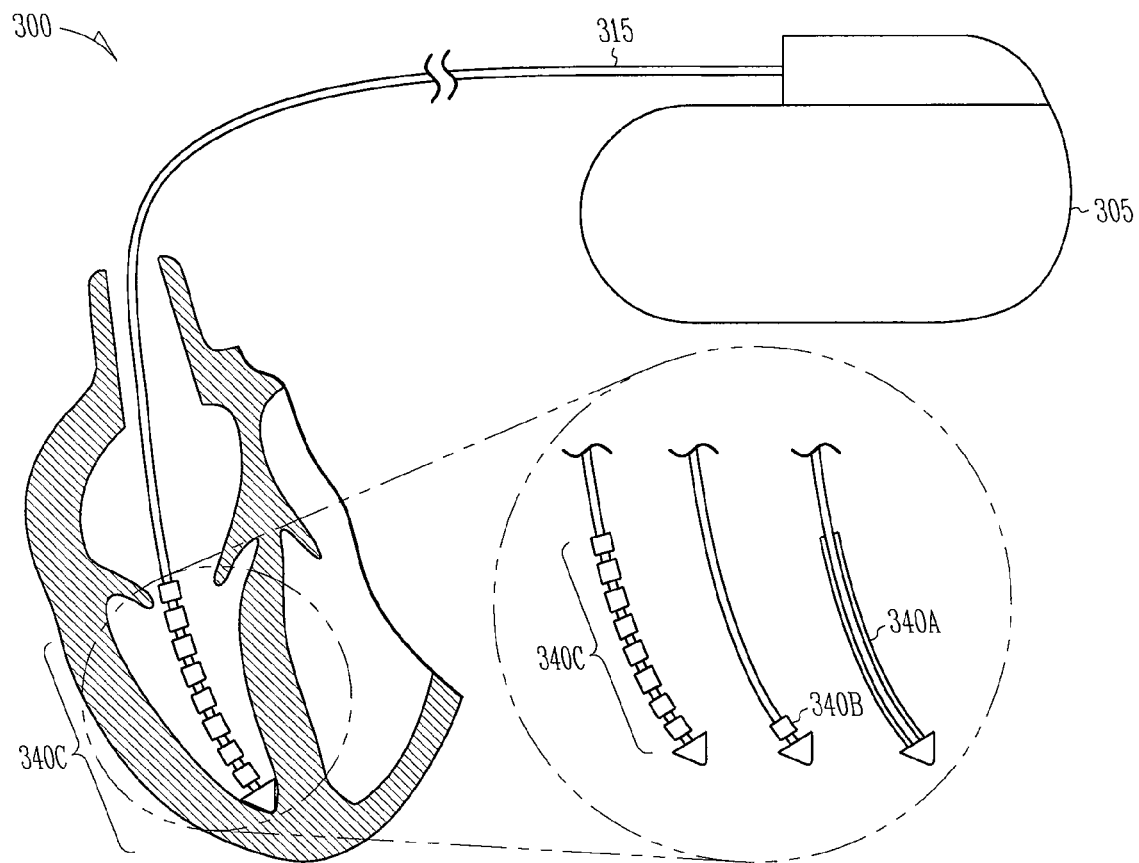
FIG. 3 is an illustration of portions of another example of a system that includes an IMD.

FIG. 3 is an illustration of portions of another example of a system 300 that includes an IMD 305 and an implantable lead 315. The implantable lead 315 includes one or more implantable acoustic transducers. FIG. 3 shows three example configurations of acoustic transducers. Implantable acoustic transducers 340A and 340B show that the transducer may be of a different size to create a different field of acoustic energy. For example, acoustic transducer 340B is a closer approximation to a point source than is acoustic transducer 340A. The implantable lead 315 may be a multi-element lead that includes multiple acoustic transducers 340C. Having two or more separately drivable acoustic transducers on a lead allows the shape of the resulting acoustic to be manipulated. Separately drivable transducers may allow different areas of the field to be canceled and/or reinforced.

Figure 4:
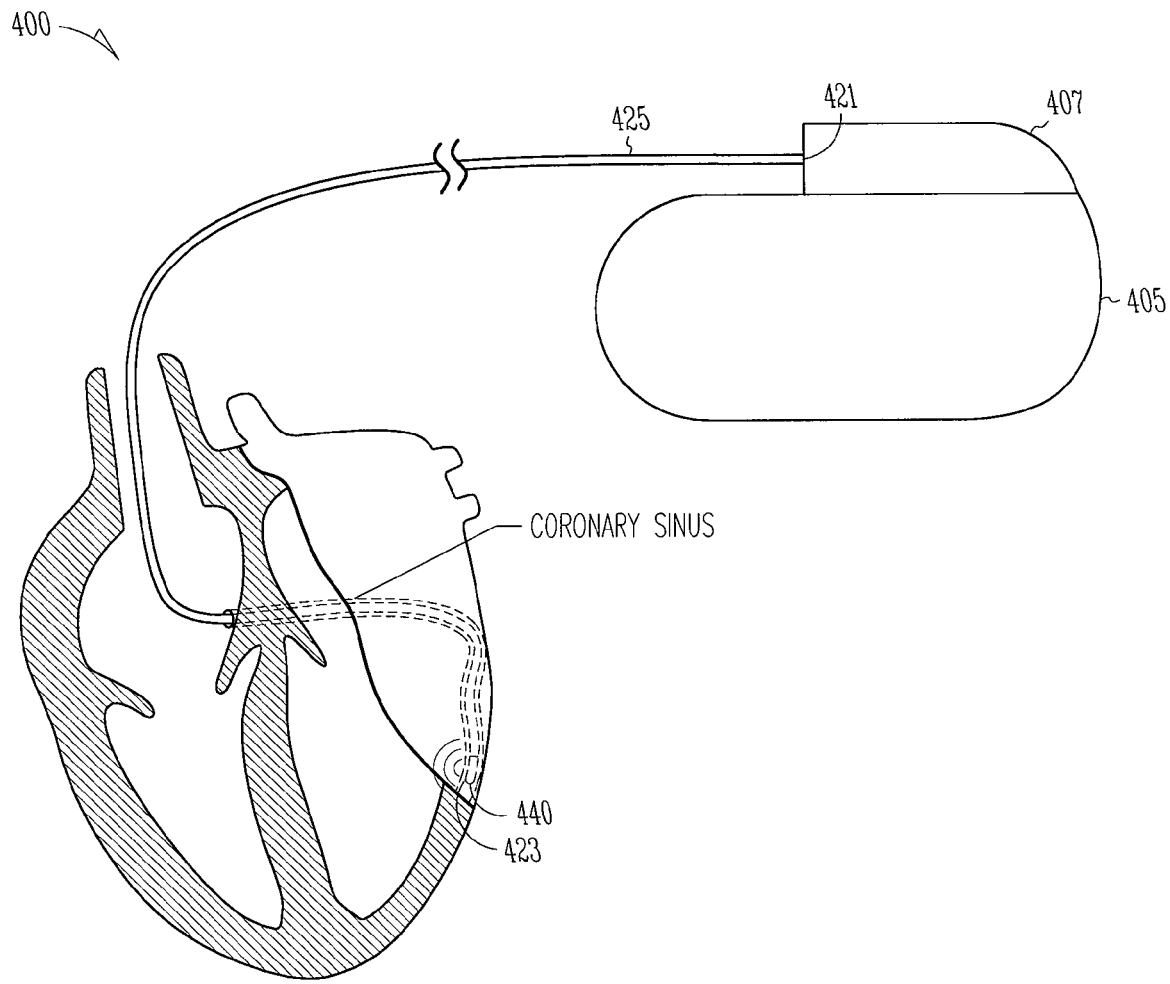
FIG. 4 is an illustration of portions of yet another example of a system that includes an IMD.

FIG. 4 is an illustration of portions of yet another example of a system 400 that includes an IMD 405. The implantable lead 425 is shaped and sized for placement in a left ventricle (LV) and has a proximal end 421 and a distal end 423. The proximal end 421 is coupled to a header connector 407. A distal end 423 is configured for placement or insertion in the coronary vein. The implantable lead 425 includes an acoustic transducer 440 at the distal end. The acoustic transducer 440 applies low frequency ultrasound energy locally to a region at or near the distal end 423 of the implantable lead. The acoustic transducer 440 may mitigate a blood vessel obstruction in the blood vessel in which it is placed in (e.g., the coronary vein in FIG. 4) or mitigate a blood vessel obstruction in an adjacent or otherwise nearby blood vessel. This is useful to place the acoustic transducer 440 in the vicinity of a stent to inhibit stent-related thrombosis. Vascular therapy sites may be those vessels typically susceptible to occlusion or with severe consequences to occlusion, such as the carotid arteries, left and right coronary arteries, and their branches for example. Vascular therapy sites may also include sites containing a second implanted device, such as a stent or another implantable lead for example.

In some examples, the IMD 405 may include one or more additional leads. In an illustrative example, the IMD 405 includes implantable lead 425 having an acoustic transducer 440 and an additional implantable lead, such as implantable lead 215 having acoustic transducer 240 in FIG. 2. The acoustic transducers 240, 440 may be independently or simultaneously activated to provide low frequency acoustic energy.

Figure 5:
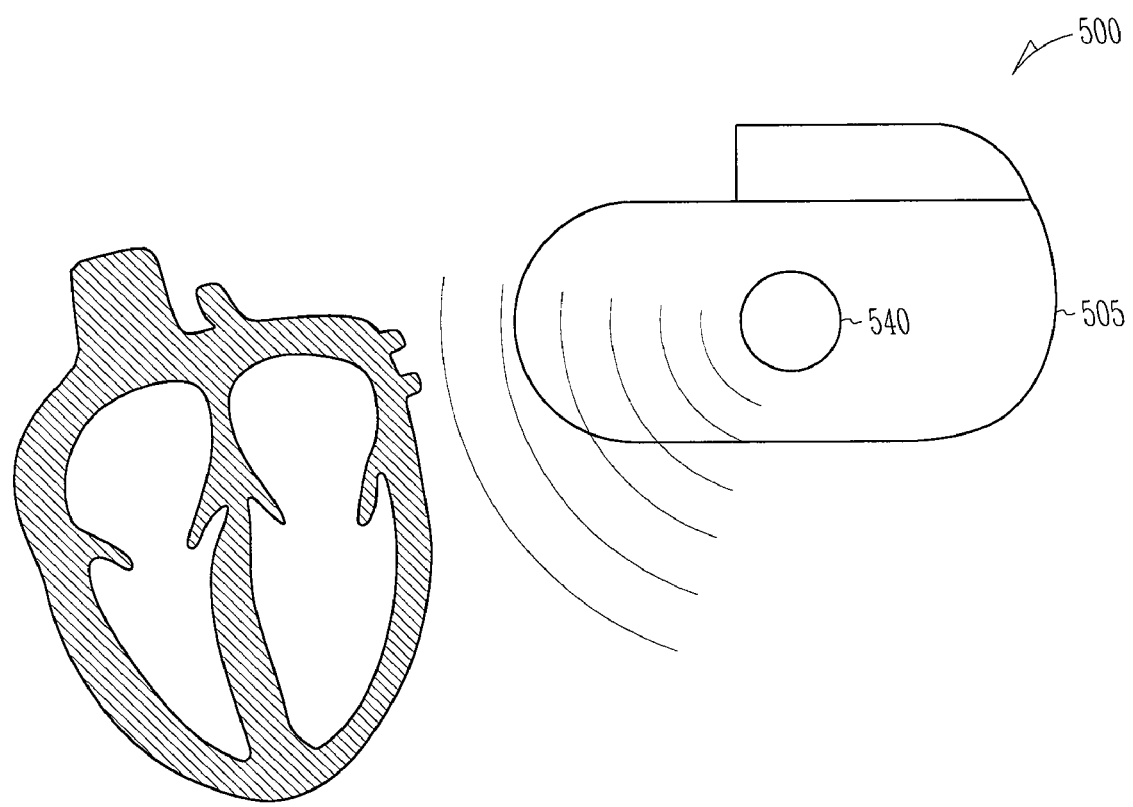
FIG. 5 is an illustration of portions of an example of a system that includes an IMD having an acoustic transducer.

FIG. 5 is an illustration of portions of a further example of a system 500 that includes an IMD 505. The apparatus includes an acoustic transducer 540 mounted on or incorporated into the can. The ultrasonic energy radiates from the acoustic transducer and the acoustic transducer 540 applies low frequency ultrasound energy globally to the thorax region of a patient to cover a larger area. The ultrasound field may be semi-directional or omni-directional. The apparatus 500 may be a stand alone device or be included in an IMD having multiple functions.

Figure 6:
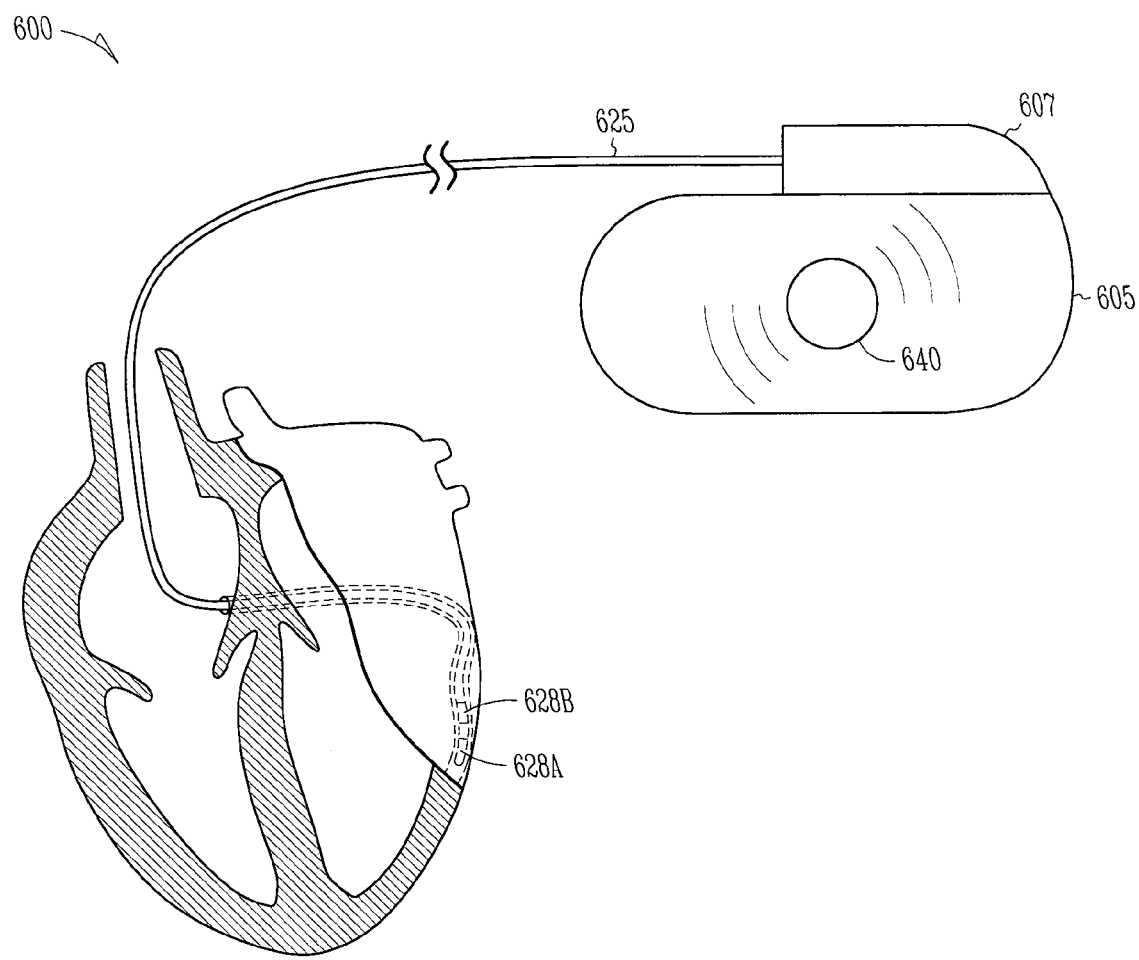
FIG. 6 illustrates portions of another example of a system that includes an IMD having an acoustic transducer.

This is shown in FIG. 6, which illustrates portions of another example of a system 600 that includes an IMD 605 having an acoustic transducer 640 mounted on or incorporated into the can. The IMD 605 is a multiple function device. Examples include a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies.

In the example shown, the apparatus 600 is used to treat a cardiac arrhythmia and includes an implantable lead such as an LV lead 625. The LV lead 625 may include pacing or sensing electrodes. The LV lead 625 may include an LV ring or tip electrode 628A and an LV ring electrode 628B to form a bipolar electrode pair.

The LV lead 625 may be used to focus the ultrasound energy from the acoustic transducer 640. The presence of the LV lead 625 may cause the ultrasound field in the vicinity of the lead to be stronger than if the lead was not there. This is useful to inhibit blood vessel obstructions that may develop due to the presence of an implantable lead. The ultrasound energy from the acoustic transducer 440 may focus on the distal tip of the lead. This allows the lead tip to be used as a target for the ultrasound energy field. The lead tip may then be placed in a region where there is a higher probability of having an obstruction form.

During implantation of cardiac rhythm management (CRM) systems, it is a common procedure for the physician to place an implantable lead by inserting a stiff guidewire or stylette through the center of the lead and then to "snake" the lead though a predetermined path to the heart.

Figure 7:
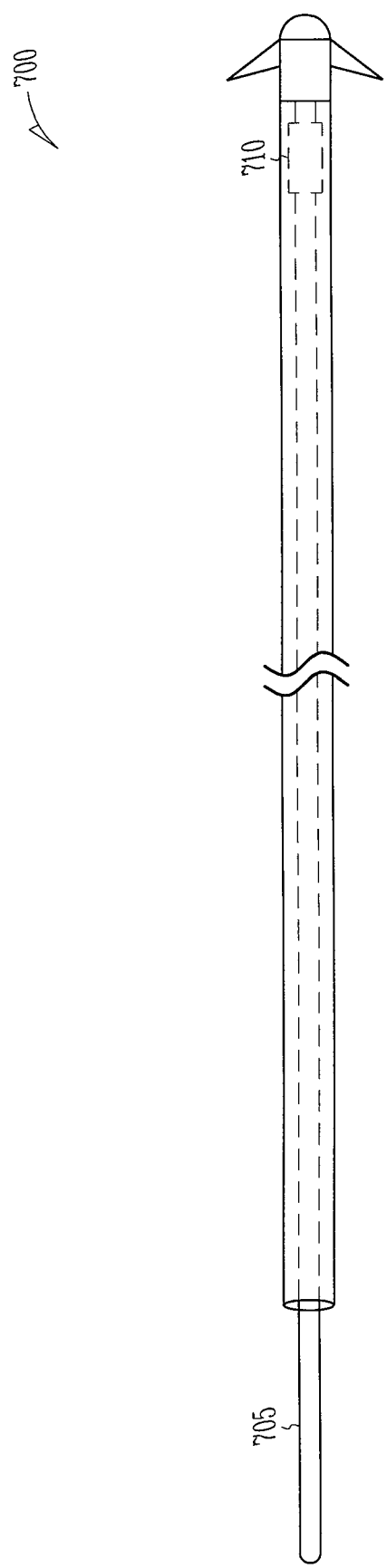
FIG. 7 is an illustration of portions of an implantable medical lead.

FIG. 7 shows an example of a portion of an implantable cardiac lead 700 with a placement guidewire 705 inserted in the lead 700. Often cardiac leads are implanted by using a guidewire to guide them through blood vessels into one or more chambers of the heart and then the guidewire is removed. In some examples, to monitor the acoustic energy present at the distal end of the cardiac lead 700 when it is implanted, the placement guidewire 705 includes an acoustic energy sensor 710 that can be temporarily positioned within the implantable cardiac lead 700. An example of an acoustic energy sensor is a piezoelectric crystal. Because a piezoelectric crystal converts mechanical energy into an electrical signal, the guidewire with the piezoelectric crystal acts as a sensor to detect the acoustic energy from the acoustic transducer 640 of FIG. 6. This allows the position or orientation of the IMD 605 to be modified during an implant procedure to maximize the acoustic energy at the implanted cardiac lead 700. Another example of an acoustic energy sensor is another ultrasonic transducer. In some examples, the acoustic energy sensor 710 is part of the implantable cardiac lead 700.

In certain examples, the acoustic transducer 640 of FIG. 6 to deliver acoustic energy is included in an implantable lead (e.g., acoustic transducer 240 on RV lead 215 in FIG. 2) instead of being included in the can of the IMD 605. In certain examples, the apparatus 600 includes an acoustic transducer 640 mounted on or incorporated into the can in addition to an acoustic transducer included in an implantable lead.

Figure 8:
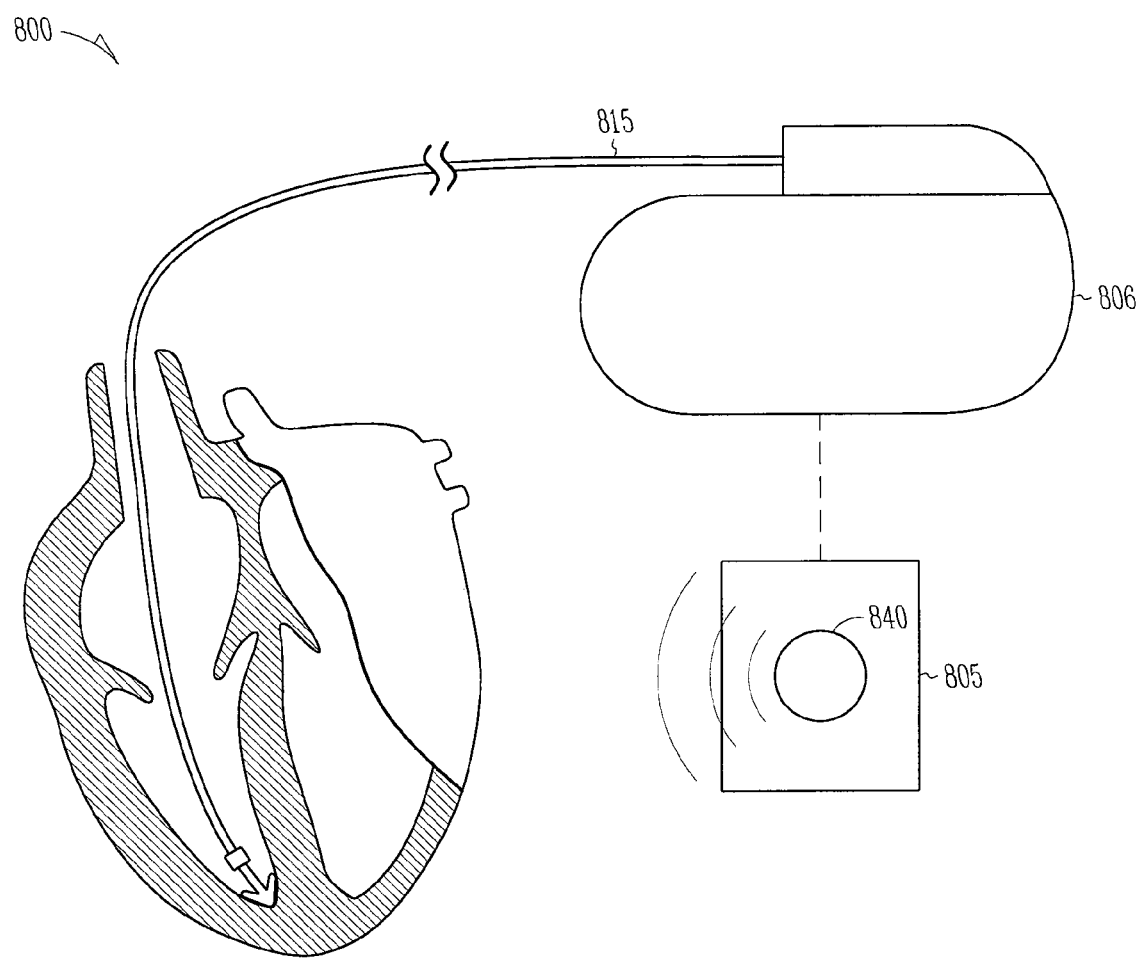
FIG. 8 is an illustration of portions of an example of a system that includes a first IMD having an acoustic transducer and a second IMD.

FIG. 8 is an illustration of portions of an example of a system 800 that includes a first IMD 805, having an acoustic transducer 840 mounted on or incorporated into the can, and includes a second IMD 806. In the example shown, the second IMD 806 is used to treat a cardiac arrhythmia and includes an implantable lead such as an RV lead 815. The first IMD 805 and the second IMD 806 communicate wirelessly, such as by radio frequency (RF) or other telemetry method. In some examples, the first IMD receives the indication of the patient condition associated with development of a blood vessel obstruction from the second IMD 806.

Figure 9:
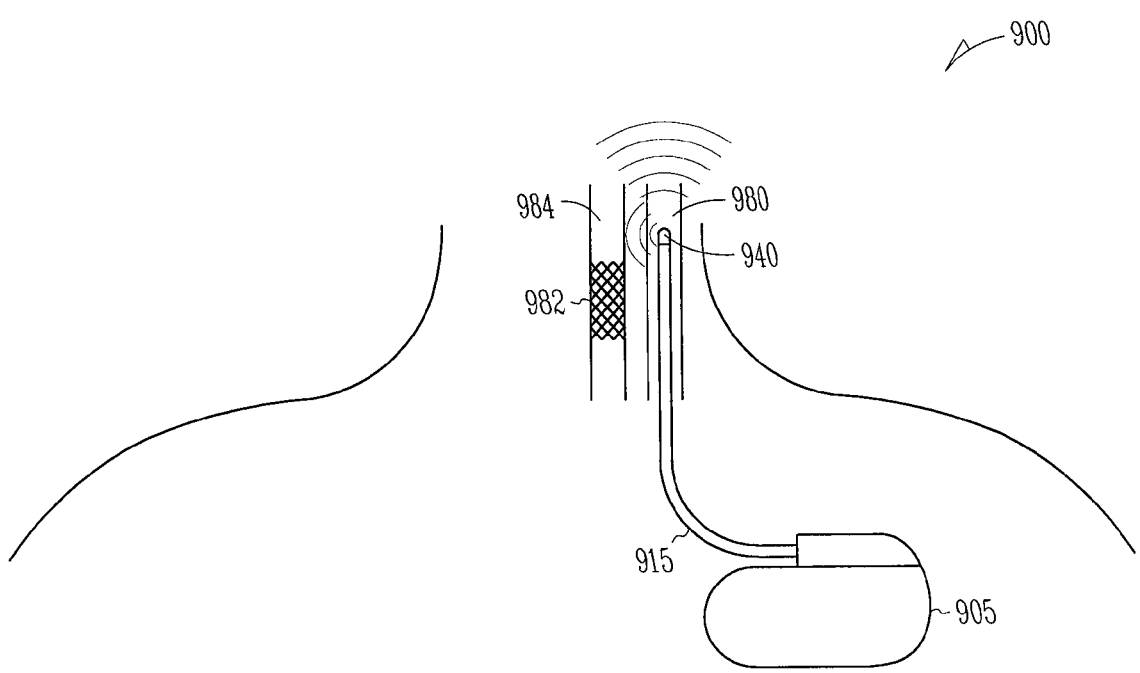
FIG. 9 is an illustration of portions of a further example of a system that includes an IMD.

FIG. 9 is an illustration of portions of still a further example of a system 900 that includes an IMD 905. The IMD 905 is coupled to an implantable lead 915 shaped and sized for placement internal to a vein 980 in the neck region of the patient, such as the jugular vein for example. The implantable lead 915 includes an implantable acoustic transducer 940. In some examples, the acoustic transducer 940 applies ultrasound energy globally to a region that includes the neck and head of the patient to mitigate any blood vessel obstruction in the neck and/or head region. In some examples, the acoustic transducer 940 applies localized ultrasound energy near the vein region where the acoustic transducer 940 is placed. FIG. 9 shows a stent 982 placed in a carotid artery 984 of the patient. Placing the acoustic transducer 940 in a vein near the carotid artery 984 is useful to inhibit stent-related thrombosis.

Figure 10:
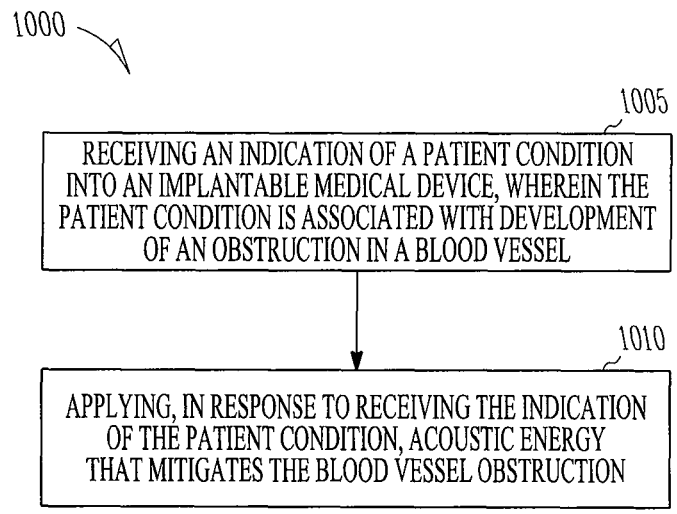
FIG. 10 is a flow diagram of a method of promoting adequate blood flow in blood vessels.

FIG. 10 is a flow diagram of a method 1000 of promoting adequate blood flow in blood vessels. At block 1005, an indication of a patient condition is received into IMD. In some examples, the IMD is configured for placement in a thorax region of the patient. The patient condition is associated with a development of a blood vessel obstruction. At block 1010, in response to receiving the indication of the patient condition, applying, acoustic energy is applied that mitigates the blood vessel obstruction using the IMD.

As described previously in regard to FIG. 1, the controller circuit 150 receives an indication of a patient condition associated with a development of a blood vessel obstruction. Atrial fibrillation is a patient condition that may lead to development of an obstruction in a blood vessel. In some examples, the IMD 105 includes a detection circuit 160 and a diagnostic sensor 175. The controller circuit 150 receives the indication of the patient condition from the detection circuit 160. In certain examples, the detection circuit 160 includes an atrial fibrillation detection circuit and the diagnostic sensor 175 includes one or more implantable electrodes. The IMD 105 includes an implantable cardiac lead configured for placement in an atrium, such as in the right atrium (RA) near the atrial septum or in the atrial appendage. The RA lead may include a pair of bipolar electrodes to sense intrinsic cardiac signals.

The electrical activity of a heart experiencing atrial fibrillation as sensed in or near the atria is distinctly different than that for normal sinus rhythm. The beginning of a cardiac cycle in normal sinus rhythm is initiated by a P-wave which is normally a small positive wave. The R-wave is associated with ventricular activations of the heart cardiac cycle. During normal sinus rhythm or other organized rhythms, there are discernible R and/or P-waves and long portions of the cardiac cycles when there is little if any discernible atrial activity. In contrast, during atrial fibrillation, there are no discernible P-waves and because the atria are in an unstable or fibrillating condition, there is detectable activity even during those portions of a cardiac cycle when there is little or no atrial activity during normal sinus rhythm or other organized rhythms. A description of systems and methods to detect atrial fibrillation is found in Kim et al., U.S. Pat. No. 5,486,199, "System and Method for Reducing False Positives in Atrial Fibrillation Detection," filed on Jul. 20, 1994, which is incorporated herein by reference.

Ischemia is a patient condition associated with development of an obstruction in a blood vessel. In certain examples, the detection circuit 160 includes an ischemia detection circuit. Evidence of myocardial ischemia in a patient can become manifest in various ways. Occurrences of coronary blood flow occlusion typically result in an immediate increase in heart rate and a decrease in myocardial shortening, particularly in an ischemic heart-wall segment. Dyssynchrony in ventricular contractions also often occurs. Sometimes, abnormalities are detectable in an electrocardiograph (ECG) within thirty seconds to one minute after the occlusion. Myocardial ischemia depresses the peak negative rate of change of pressure (dP/dt) in the left ventricle (LV) and also depresses the LV peak positive dP/dt. Myocardial ischemia may eventually lead to elevation of the S-T segment of the QRST cardiac activation sequence.

A plurality of diagnostic sensors can be used to detect a series of events related to ischemia. The probability that a patient has indeed experienced an ischemic event increases with the number of events in the series that are detected. Implantable CRM devices are sometimes equipped with implantable sensors that have the capability to detect various physiological variables associated with cardiac and pulmonary function. These sensors are typically used in applications such as rate responsive pacing and advanced patient management functions, such as remote patient monitoring and remote triggering of device therapy for example. Because myocardial ischemia can result in changes in the various physiological variables, these sensors may also be used for early detection of myocardial ischemia. A description of systems and methods to detect ischemia is found in Zhang et al., U.S. patent application Ser. No. 11/625,045, "Heart Attack Detector," filed Jan. 19, 2007, which is incorporated herein by reference.

The electrical impedance of a cardiac region will increase as perfusion decreases in the region due to an occlusion. Thus, a localized increase in electrical impedance is a patient condition associated with development of an obstruction in a blood vessel. An impedance signal indicative of a cardiac local impedance of a cardiac region can be sensed by bipolar electrodes, such as bipolar electrodes on a pacing or defibrillation lead, placed in or near that cardiac region. The diagnostic sensor 175 includes the bipolar electrodes and the detection circuit 160 includes an impedance measuring circuit. The sudden change in impedance due to the decrease in perfusion in or near the affected cardiac region may be detected using the electrodes. A description of devices and methods to sense local impedance is found in Ni et al., U.S. patent application Ser. No. 11/690,700, entitled "Closed Loop Resynchronization Therapy for Mechanical Dyssynchrony," which is incorporated by reference.

In some examples, the diagnostic sensor 175 includes an acoustic (e.g., ultrasonic) energy sensor. The detection circuit 160 uses acoustic energy at a first frequency to detect the patient condition, and acoustic energy at a second (e.g., lower) frequency for therapy for the patient condition. For example, the application of acoustic energy at the first frequency may be used in order to detect the condition. When the controller circuit 150 receives an indication that the condition is present from the detection circuit 160, the controller circuit 150 initiates the application of acoustic energy at a lower second frequency to mitigate the blood vessel obstruction. The control and activation of the diagnostic transducer may be by elements common to the acoustic transducer 140 (e.g., controller circuit 150 and interface circuit 145) or dedicated elements (not shown). In certain examples, acoustic transducer 140 provides both the low frequency acoustic energy for therapy and is connected to detection circuit 160 for use in the diagnostic sensor. Thus, acoustic transducer 140 serves both diagnostic and therapy functions.

A localized decrease in blood flow velocity is a patient condition associated with development of an obstruction in a blood vessel. In some examples, the detection circuit 160 includes a blood flow velocity measurement circuit. In certain examples, the blood flow velocity measurement circuit includes a Doppler ultrasonic transducer included in an implantable lead as the diagnostic sensor 175 and a Doppler circuit to measure blood flow. Ultrasonic energy having a frequency of 2 MHz (megahertz) is generated using the blood flow velocity measurement circuit or a different circuit. The Doppler circuit receives ultrasonic information (e.g., wave or phase information) having a frequency of 2 MHz or higher to measure the blood velocity using the Doppler Effect. The blood flow velocity measurement circuit generates a blood flow velocity measurement from the ultrasonic information. The detection circuit 150 may include a signal processor to generate the blood flow velocity measurement. A description of measuring blood flow velocity using the Doppler Effect is found in Ferek-Petric et al., U.S. Pat. No. 5,243,976, filed Mar. 25, 1991, which is incorporated by reference.

The detection circuit 160 receives a blood flow velocity measurement. If the blood flow velocity measurement indicates that localized blood flow has decreased below a blood flow velocity threshold, the controller circuit 150 initiates application of acoustic energy at a lower second frequency to mitigate a possible blood vessel obstruction.

As described previously, the controller circuit 150 may receive an indication of a patient condition associated with development of a blood vessel obstruction from a second device 165. The second device may be an external device or the second device 165 may be a second separate IMD. In some examples, the controller circuit 150 may receive the indication as a command to begin applying acoustic energy to mitigate the blood vessel obstruction.

In certain examples, the controller circuit 150 receives an indication of atrial fibrillation from the second device 165. An example of the second device 165 is a separate implantable cardiac rhythm management (CRM) device. In certain examples, the controller circuit 150 receives an indication of ischemia from the second device 165. The second device 165 may be an implantable CRM device that detects ischemia. The second device 165 may be an external device that detects ischemia, or may be an external communication device, such as a repeater for example, that relays the information that the patient has developed ischemia.

In certain examples, the controller circuit 150 receives an indication of a decrease in blood velocity from the second device 165. The second device 165 may be another implantable device that detects that blood flow velocity has deceased below a threshold velocity or an external device that communicates the indication.

Thrombosis is a patient condition associated with development of an obstruction in a blood vessel. In certain examples, the controller circuit 150 receives an indication of thrombosis from the second device 165. An increase in blood viscosity is a patient condition associated with development of an obstruction in a blood vessel. In certain examples, the controller circuit 150 receives an indication of an increase in blood viscosity from the second device 165.

A decrease in regional perfusion is a patient condition associated with development of an obstruction in a blood vessel. In some examples, the controller circuit 150 receives an indication of a decrease in regional perfusion from the second device 165.

Figure 11:
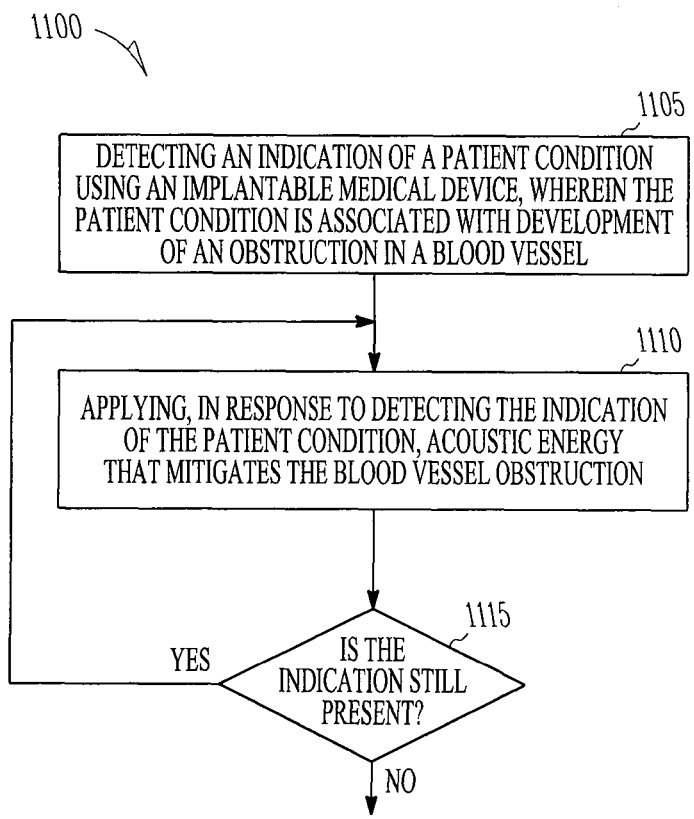
FIG. 11 is a flow diagram of another method of promoting adequate blood flow in blood vessels.

FIG. 11 is a flow diagram of another example of a method 1100 of promoting adequate blood flow in blood vessels. At block 1105, an indication of a patient condition associated with development of an obstruction in a blood vessel is detected using an implantable medical device. Examples of such a patient condition include atrial fibrillation, thrombosis, ischemia, a decrease in blood velocity, an increase in blood viscosity, and a decrease in regional perfusion. The patient condition is detected using any of the methods described herein.

At block 1110, in response to detecting the indication of the patient condition, acoustic energy is applied that mitigates the blood vessel obstruction. In some examples, the acoustic energy mitigates the blood vessel obstruction by thrombolysis. In some examples, the acoustic energy mitigates the blood vessel obstruction by inducing vasodilation.

At block 1115, the acoustic energy is continued to be applied while the detected patient condition continues to be present. Thus, the method provides a feedback system that continues to apply the low frequency acoustic energy while the patient condition is detected. The acoustic energy is removed once detection of the condition ends.

In some examples, the controller circuit 150 may receive the indication of the patient condition as a command to begin applying acoustic energy from an external device to provide on-demand operation. The command from the external device may be triggered by a patient, a physician, or care giver as may be necessary.

The devices and methods described herein may be applied to patients who are known to be, or suspected to be, susceptible to ischemia because of thrombus formation in critical arteries, or who are known to have chronic problems with thrombosis in veins. Such patients may have coronary artery disease and have undergone an angioplasty, stent, or coronary bypass graft procedure, or are candidates for such procedures. The patients may also include those with a family history of coronary artery disease. The devices and methods may be applied to maintain patency of cranial arteries and to prevent strokes in patients with a history of strokes and transient ischemic attacks. An acoustic transducer may be located to apply therapy to the affected vessel or vessels or region containing the vessels. The therapy may be activated periodically as a preventative or restorative therapy or upon demand if ischemia is detected.

Low frequency ultrasound may be used either by itself or in combination with blood clot dissolving drugs or recombinant tissue plasminogen activators (tPAs). In combinational therapy, ultrasound may mitigate clot dissolution by increasing the effectiveness of pharmatherapy because the ultrasound therapy allows the drug to penetrate the blood clot quickly. Combinational therapy may reduce the required drug dosage and thereby reduce the side effects of the drugs, such as systemic hemorrhages.

In some examples, the IMD 105 is a combination device that delivers both drug therapy and acoustic energy therapy. In some examples, a patient may initiate delivery of the acoustic energy by sending a command from an external device when the patient takes drug therapy. In certain examples, when the detection circuit 160 detects a patient condition associated with development of a blood vessel obstruction, the controller circuit 150 initiates delivery of the acoustic energy and communicates that a patient condition was detected to an external device. The external device provides an indication to the patient to take the drug therapy while the acoustic energy is delivered. The indication from the external device may be an auditory tone or message, or a visual message on a display included in the external device.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. Apparatus comprising:
   an acoustic transducer configured to be implanted in a thoracic blood vessel or heart;
   an acoustic transducer interface circuit communicatively coupled to the acoustic transducer; and
   a controller circuit, communicatively coupled to the acoustic transducer interface circuit, wherein the controller is configured to:
   enable detection of a patient condition by initiating application of acoustic energy by the transducer at a first frequency; and
   in response to receiving an indication of the patient condition, cause the transducer to initiate delivery of acoustic energy at a second frequency configured to mitigate the blood vessel obstruction.

2. The apparatus of claim 1, including an atrial fibrillation detection circuit communicatively coupled to the controller circuit and configured to provide the indication upon detecting atrial fibrillation.

3. The apparatus of claim 1, including an ischemia detection circuit communicatively coupled to the controller circuit and configured to provide the indication upon detecting ischemia.

4. The apparatus of claim 1, wherein the
   second frequency is a lower frequency than the first frequency.

5. The apparatus of claim 4, including a detection circuit communicatively coupled to the controller circuit, wherein the detection circuit includes a blood flow velocity measurement circuit configured to:
   receive ultrasonic information using ultrasonic energy at the first frequency; and
   generate a blood flow velocity measurement from the ultrasonic information;
   wherein the indication includes a blood flow velocity measurement that is less than a blood flow velocity threshold.

6. The apparatus of claim 1, including a detection circuit coupled to the controller circuit configured to detect the indication of the patient condition associated with a development of a blood vessel obstruction, and wherein the controller circuit is configured to apply acoustic energy while the detection circuit indicates the patient condition.

7. The apparatus of claim 1, including a communication circuit communicatively coupled to the controller circuit, wherein the controller circuit is configured to communicate with a separate second device using the communication circuit and to receive the indication from the separate second device.

8. The apparatus of claim 7, wherein the indication includes at least one of an increase in blood viscosity, thrombosis, atrial fibrillation, ischemia, a decrease in blood velocity, and a decrease in local perfusion.

9. The apparatus of claim 1, wherein the acoustic transducer is included in an implantable lead, wherein the implantable lead is configured for placement in or near a blood vessel.

10. The apparatus of claim 1, wherein the acoustic transducer is included in an implantable lead, wherein the implantable lead is configured for placement in or near a localized region of a heart.

11. The apparatus of claim 1, wherein the acoustic transducer is included in a housing of the implantable medical device.

12. The apparatus of claim 1, including an implantable lead configured for placement in or near a blood vessel, and wherein the acoustic transducer is included in a housing of the implantable medical device and delivers acoustic energy towards the implantable lead.

13. The apparatus of claim 12, wherein the implantable lead includes an acoustic energy sensor.

14. The apparatus of claim 12, including a placement guidewire configured for insertion into the implantable lead, wherein the guidewire includes an acoustic energy sensor.

15. A method comprising:
applying acoustic energy to thoracic cardiovascular tissue of a patient at a first frequency to detect a patient condition associated with a development of a blood vessel obstruction using an implantable medical device (IMD);
receiving an indication of the patient condition into the IMD; and
applying, in response to receiving the indication of the patient condition, acoustic energy at a second frequency to mitigate the blood vessel obstruction using the IMD.

16. The method of claim 15, wherein receiving the indication of a patient condition includes detecting with the IMD at least one of atrial fibrillation, a decrease in blood flow velocity, or ischemia.

17. The method of claim 15, wherein receiving the indication of a patient condition includes receiving an indication of at least one of thrombosis, an increase in blood viscosity, or a decrease in regional perfusion.

18. The method of claim 15,
wherein applying acoustic energy at a second frequency includes applying acoustic energy at a frequency, lower than the first frequency, that mitigates the blood vessel obstruction.

19. The method of claim 18, wherein:
applying acoustic energy at a first frequency includes applying ultrasound energy at a frequency greater than two megahertz (2 MHz) to measure blood flow velocity; and
wherein applying acoustic energy at a lower second frequency includes applying ultrasound energy at a frequency of about 500 kilohertz (kHz) or less to mitigate the blood vessel obstruction.

20. The method of claim 15, wherein the applying acoustic energy includes applying localized ultrasound energy to a blood vessel in the thorax region of the patient.

21. The method of claim 15, wherein the applying acoustic energy includes applying ultrasound energy locally to a region of the heart.

22. The method of claim 15, wherein the applying acoustic energy includes applying ultrasound energy globally to the thorax region.

23. The method of claim 15, wherein the applying acoustic energy includes applying localized ultrasound energy to a region containing a second separate implantable device.

24. The method of claim 15, wherein the applying acoustic energy includes initiating the applying acoustic energy by the implantable medical device using a separate second device.

25. The method of claim 15, wherein receiving the indication includes detecting the patient condition associated with a development of a blood vessel obstruction using the IMD,
wherein applying acoustic energy includes applying the acoustic energy in response to detecting the patient condition, and
wherein the method includes continuing the applying acoustic energy while the detected condition is present.

* * * * *